(12) United States Patent
Högerle

(10) Patent No.: US 12,268,375 B2
(45) Date of Patent: Apr. 8, 2025

(54) INTEGRATED POWER UNIT IPU

(71) Applicant: Aesculap AG, Tuttlingen (DE)

(72) Inventor: Roland-Alois Högerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 916 days.

(21) Appl. No.: 17/423,568

(22) PCT Filed: Jan. 14, 2020

(86) PCT No.: PCT/EP2020/050807
§ 371 (c)(1),
(2) Date: Jul. 16, 2021

(87) PCT Pub. No.: WO2020/148275
PCT Pub. Date: Jul. 23, 2020

(65) Prior Publication Data
US 2022/0117590 A1 Apr. 21, 2022

(30) Foreign Application Priority Data
Jan. 18, 2019 (DE) ...................... 10 2019 101 308.9

(51) Int. Cl.
*A61B 17/00* (2006.01)
*H02J 7/00* (2006.01)

(52) U.S. Cl.
CPC .................. *A61B 17/00234* (2013.01); *A61B 2017/00199* (2013.01); *A61B 2017/00221* (2013.01);
(Continued)

(58) Field of Classification Search
CPC .... A61B 17/00234; A61B 2017/00199; A61B 2017/00221; A61B 2017/00734; A61B 2017/00973; H02J 7/00032; H02J 7/0048
(Continued)

(56) References Cited

U.S. PATENT DOCUMENTS 5,314,407 A * 5/1994 Auth .............. A61B 17/320758
606/159
6,633,278 B1 10/2003 Hoegener et al.
(Continued)

FOREIGN PATENT DOCUMENTS

CN 104487008 A 4/2015
CN 105982702 A 10/2016
(Continued)

OTHER PUBLICATIONS

Office Action received in Japanese Application No. 2021-541177 dated Jul. 20, 2023, with translation, 7 pages.
(Continued)

*Primary Examiner* — Aaron F Roane
(74) *Attorney, Agent, or Firm* — Christopher A. Rothe; CM Law

(57) ABSTRACT

An actuating unit for or of a surgical instrument operated by an electric motor and having a switch housing. The switch housing is separate and spaced apart from the surgical instrument and includes a frame, supports for supporting the switch housing on a substrate, at least one power supply unit for supplying power to at least one motor system of a surgical instrument connected to the actuating unit, a control and monitoring device designed to carry out and/or monitor at least one function, and a cable and/or a cable connection for connecting the cable for electrically coupling the actuating unit to a surgical instrument for operating the surgical instrument.

10 Claims, 3 Drawing Sheets

(52) U.S. Cl.
CPC .............. *A61B 2017/00734* (2013.01); *A61B 2017/00973* (2013.01); *H02J 7/00032* (2020.01); *H02J 7/0048* (2020.01)

(58) Field of Classification Search
USPC .......................................................... 606/1
See application file for complete search history.

(56) References Cited

U.S. PATENT DOCUMENTS

| | | |
|---|---|---|
| 9,559,624 B2 | 1/2017 | Philipp |
| 9,619,618 B2 | 4/2017 | Ingmanson |
| 2002/0086264 A1 | 7/2002 | Okawa et al. |
| 2004/0035242 A1 | 2/2004 | Peterson et al. |
| 2006/0047200 A1 | 3/2006 | Miyazawa |
| 2007/0085496 A1 | 4/2007 | Philipp et al. |
| 2009/0205937 A1 | 8/2009 | Kuehner et al. |
| 2010/0241151 A1 | 9/2010 | Rickard |
| 2012/0011293 A1 | 1/2012 | Cheng et al. |
| 2013/0253552 A1* | 9/2013 | Schoenle ....... A61B 17/320758 606/159 |
| 2014/0371770 A1 | 12/2014 | Schoene et al. |
| 2016/0073855 A1 | 3/2016 | Farr et al. |
| 2016/0174018 A1 | 6/2016 | Schönewerk |
| 2016/0249915 A1* | 9/2016 | Beckman ............ A61B 17/068 227/175.1 |
| 2016/0375273 A1 | 12/2016 | Hirai et al. |
| 2017/0007219 A1 | 1/2017 | Bucina et al. |
| 2017/0360466 A1 | 12/2017 | Brown et al. |
| 2018/0043146 A1 | 2/2018 | Vescovi |
| 2018/0055591 A1 | 3/2018 | Bonny et al. |
| 2018/0070943 A1 | 3/2018 | Malinouskas et al. |
| 2018/0341400 A1 | 11/2018 | Kim et al. |
| 2020/0253628 A1 | 8/2020 | Brown et al. |

FOREIGN PATENT DOCUMENTS

| | | |
|---|---|---|
| CN | 107106201 A | 8/2017 |
| DE | 102005029458 A1 | 12/2006 |
| DE | 102013114918 A1 | 7/2015 |
| EP | 1326565 A1 | 7/2003 |
| EP | 1567063 B1 | 8/2005 |
| EP | 1698373 A1 | 9/2006 |
| EP | 3070627 A1 | 9/2016 |
| EP | 3032513 B1 | 8/2017 |
| JP | 2001142003 A | 5/2001 |
| JP | 2001525566 A | 12/2001 |
| JP | 2002143183 A | 5/2002 |
| JP | 2006068220 A | 3/2006 |
| JP | 2007029451 A | 2/2007 |
| JP | 2008546503 A | 12/2008 |
| JP | 2011206596 A | 10/2011 |
| JP | 2011218164 A | 11/2011 |
| JP | 2013536613 A | 9/2013 |
| JP | 2016174896 A | 10/2016 |
| JP | 2017018598 A | 1/2017 |
| JP | WO2016167195 A1 | 5/2017 |
| WO | 0121056 A2 | 3/2001 |
| WO | 2008092042 A2 | 7/2008 |
| WO | 2016100522 A1 | 6/2016 |
| WO | 2016161322 A1 | 10/2016 |
| WO | 2017189606 A1 | 11/2017 |

OTHER PUBLICATIONS

Translation of Search Report received in Japanese Application No. 2021-541177, dated Jul. 28, 2023, with translation, 11 pages.
Office Action received in U.S. Appl. No. 17/415,785 dated Jan. 18, 2024, 28 pages.
Office Action received in Chinese Application No. 202080008085.1 dated Mar. 1, 2024, with translation, 14 pages.
Office Action received in Japanese Application No. 2021-535979 dated Feb. 20, 2024, with translation, 10 pages.
Office Action received in Japanese Application No. 2021-54-117 dated Mar. 5, 2024, with translation, 8 pages.
Search Report received in German Application No. 10 2019 101 308.9 dated Sep. 13, 2019, with translation, 19 pages.
Search Report received in International Application No. PCT/EP2020/0050807 dated Mar. 30, 2020, 5 pages.
Written Opinion received in International Application No. PCT/EP2020/0050807 dated Mar. 30, 2020, with translation, 11 pages.
Office Action received in Japanese Application No. 2021-535979 dated Jul. 21, 2023, with translation, 32 pages.
International Search Report received in International Application No. PCT/EP2019/086567 dated Mar. 26, 2020, with translation, 7 pages.
Search Report received in German Application No. 10 2018 135 504.0 dated Nov. 12, 2019, with translation, 19 pages.
Written Opinion received in International Application No. PCT/EP2019/086567 dated Mar. 26, 2020, with translation, 17 pages.
Office Action received in Chinese Application No. 202080008085.1 dated Sep. 3, 2024, with translation, 16 pages.

* cited by examiner

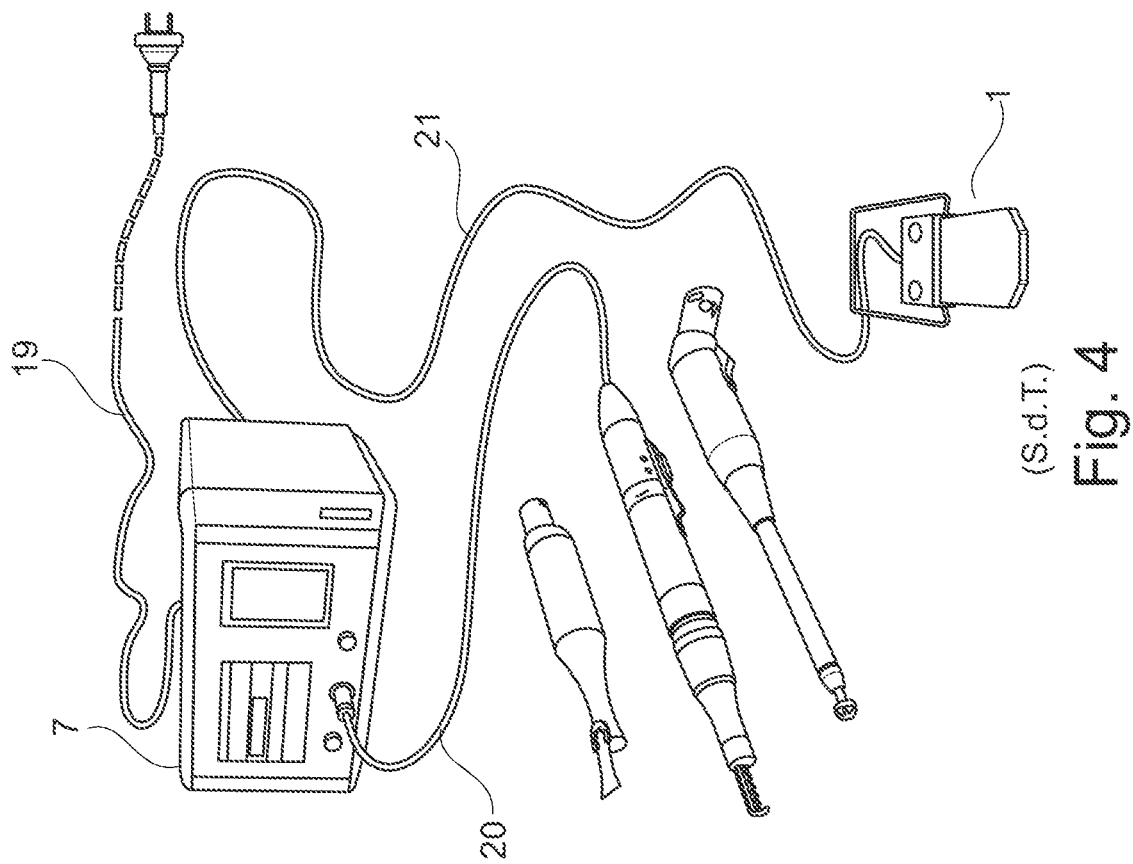
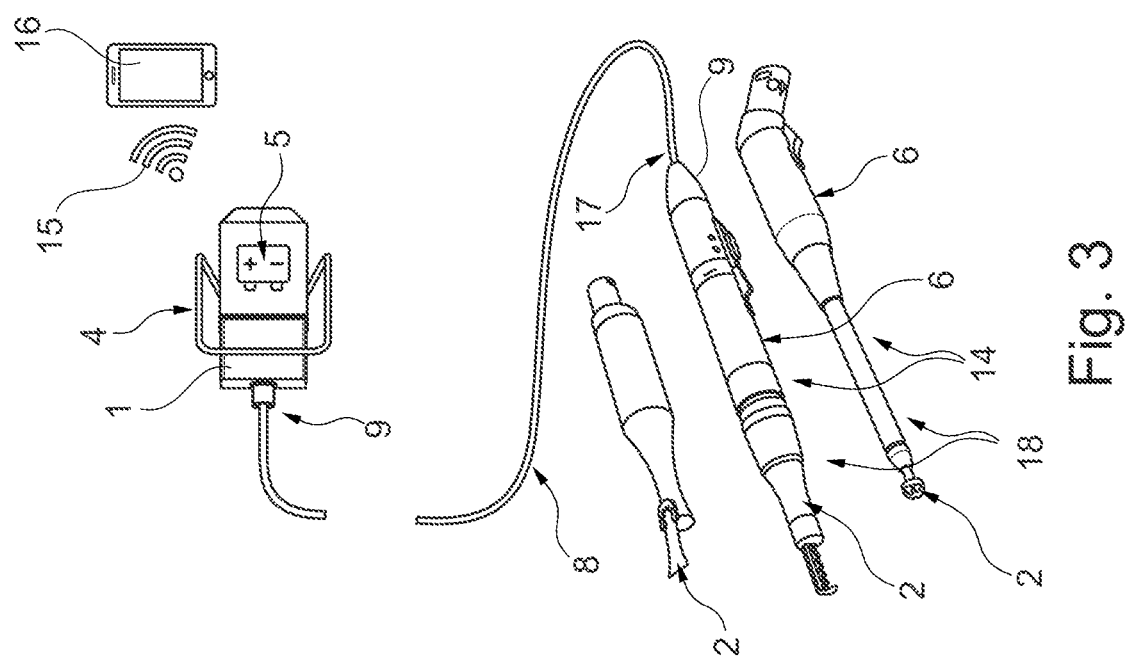
Fig. 3
Fig. 4 (S.d.T.)

INTEGRATED POWER UNIT IPU

CROSS-REFERENCE TO RELATED APPLICATIONS

This application is the United States national phase entry of International Application No. PCT/EP2020/050807, filed Jan. 14, 2020, and claims the benefit of priority of German Application No. 10 2019 101 308.9, filed Jan. 18, 2019. The contents of International Application No. PCT/EP2020/050807 and German Application No. 10 2019 101 308.9 are incorporated by reference herein in their entireties.

FIELD

The present disclosure relates to an actuating unit, in particular a foot-operated switch unit or a hand-operated switch unit for an or of an electromotively-operated surgical instrument preferably of the minimally invasive type.

BACKGROUND

Up to now, at least three lines/cables have been necessary to operate a motor system. In this case, a first line serves as a power supply line and supplies a control and monitoring unit with power from a mains connection. A second line is used to connect the control and monitoring unit to the motor system attached to a handpiece. This line serves both as a power supply line and as a communication connection for transmitting data and/or operating parameters. A third line is used to connect a foot switch or hand switch to the control and monitoring unit.

Both the aforementioned second line and the third line run from the patient area, which is also referred to hereinafter as the sterile area, across the operating room. This poses a considerable risk, such as a defect caused by a cart and/or hospital bed rolling over the cable or the like. Furthermore, such lines form a bridge between the sterile area and a non-sterile area and pose a fall hazard for clinical staff. Likewise, the use of such lines can lead to decoupling/uncoupling during operation. Another disadvantage of these lines is the required length of the respective lines/cables. The first line already requires a length of at least 1.5 to 5 m. The second line has a length of at least 4 m and the third line measures at least 5 m. Apart from the disadvantages described above for the personnel and/or the patient, the respective cables can cause far-reaching technical problems, such as in the area of EMC (electromagnetic compatibility) and/or signal transmission of the motor current and/or data transmission between handpiece and control device, etc.

Actuating units are already known from the prior art. From DE 10 2013 114 918 A1, for example, a medical switch, in particular a foot-operated switch, having a switch base and a removable actuating element for actuating the switch is known, wherein the actuating element is mounted such that it can be positioned relative to the switch base between a first switching position and a second switching position via at least one axis element, and a securing means is provided, via which the actuating element can be brought into a release position relative to the switch base at least in the first switching position and the second switching position on the switch base, and in this case a relative positioning of the actuating element and the securing means occurs, so that the actuating element can be removed from the switch base.

From DE 10 2005 029 458 A1, an actuating device for electromedical devices, in particular foot-operated switches, is known having a bottom part, at least one pedal part which is pivotally connected to the bottom part, and at least one switching element 12 which can be actuated by the pedal part.

WO 01/21056 A2 describes a surgical tool station having several tools, wherein a separate foot-operated switch is arranged under the operating table for each tool.

EP 3 032 513 B1 describes a pairing method for wireless communication connection of an operating unit, in particular a foot-operated switch device, of a medical control unit, in particular a foot control unit, to a control device of the medical control unit, wherein the operating unit and the control device communicate wirelessly with each other. It also relates to a medical control unit, in particular a foot control unit with an operating unit, in particular a foot-operated switch device, and a control device which can be connected to the latter by wireless communication, wherein the operating unit has at least two operating elements, the respective actuation of which by the user causes a control signal to be sent by the control device to the medical device for controlling the latter.

EP 1 567 063 B1 relates to foot-operated switches used in the operation of microsurgical systems. A microsurgical system is provided with a computer and a foot-operated switch functionally coupled to the computer.

EP 1 326 565 B1 relates to a microsurgical control system having a computer, a foot-operated switch functionally coupled to the computer, and a touch screen display functionally coupled to the computer.

Thus, in the prior art, it is disadvantageous that, for example, the use of a radio foot-operated switch only replaces the aforementioned third line, which is not optimal in terms of size, cost or reliability. In addition, the cable/lines according to the aforementioned first and second line still form a bridge from the sterile area to the non-sterile area.

Furthermore, it is disadvantageous that the products available on the market use a battery pack consisting of several batteries connected in series. This is necessary, since normally each individual battery supplies about 1.3 VDC. In order to achieve the nominal voltage for the various devices or instruments, such individual batteries have to add up their voltage. This condition results in heavy and expensive power modules.

When accumulators are used, the size of the motor-driven surgical system is unacceptable and there is insufficient performance and reliability.

SUMMARY

The present invention is therefore based on the object of providing an actuating unit for a surgical instrument or an electromotively-operated surgical instrument which avoids or at least improves the disadvantages of the prior art.

The core of the present invention is to provide an actuating unit with which an electromotively-operated surgical instrument can be operated without the need for a connection from the sterile area to the non-sterile area. In other words, neither the actuating unit nor the electromotively-operated surgical instrument is connected via a line/cable to an external control and/or monitoring unit located outside the sterile area.

The object of the invention is solved in that an actuating unit, in particular a foot-operated switch unit or hand-operated switch unit, having a switch housing which is separate from and spatially spaced apart from a surgical instrument and which is configured or provided with a frame, bases or similar supporting means for supporting the switch housing on a surface, preferably a bottom, or fastening means for fastening to a fastening base, such as an operating table or a robot arm. The top side of the switch housing also serves as an accelerator pedal, and is actuated by pressing the top side of the switch housing in the direction of the bottom/surface/fastening base. Furthermore, the actuating unit is formed with at least one power supply unit, preferably an energy storage unit, which is configured for a power supply of at least one electric motor of a surgical instrument connected to the actuating unit. In addition, the actuating unit has a control and monitoring device configured to perform and/or monitor at least one of the following functions.

The control and monitoring unit can monitor a state of charge of the energy storage unit and/or switch on/off an energy supply to a surgical instrument connected thereto and/or receive data from the actuating unit and/or send data to the actuating unit and/or output and/or receive operating parameters and/or operating signals to and/or from a surgical instrument connected thereto, preferably with respect to its electric motor, and/or store data and/or operating parameters.

Furthermore, the actuating unit is designed with a cable and/or a cable connection for connecting the cable for electrically coupling the actuating unit to a surgical instrument for operating its electric motor via the power supply unit integrated in the actuating unit and preferably for transmitting the data and/or operating parameters, in particular safety-relevant electrical signals and data.

In other words, this means that the entire supply to the motor and the communication between the control and/or monitoring unit takes place/is carried out via precisely one cable, which connects the actuating unit and the electromotively-operated surgical instrument with each other. Thus, the solution of the present object realizes that no cable/lines form a bridge into the non-sterile area. The entire assembly is therefore in the sterile area.

It is preferred if the control and monitoring device is an IPU unit or is configured as an IPU unit with an energy storage unit, a signal-generator device, a motor energization device, a data acquisition device and a sending unit, and the IPU unit is integrated in the switch housing of the actuating unit. In other words, this means that the entire power supply of the motor as well as new functions are installed/arranged in the actuating unit, in particular the foot-operated switch or the hand-operated switch. Thus, the energy storage unit is integrated as a power supply in the switch housing and can supply both the electromotively-operated surgical instrument with its motor system and all other components of the IPU integrated in the switch housing with energy.

For example, the integrated signal generator outputs a signal which, for example, specifies clockwise rotation of the electric motor. In the same way, the motor current can be controlled and, if necessary, can also be automatically adapted to the respective application part/handpiece connected to the motor system. The data acquisition installed in the actuating part is used, for example, to record reprocessing cycles, a reprocessing duration, washing cycles and/or the maintenance status of the motor. The sending unit sends data and/or operating parameters to an external unit, such as a smartphone or charging station.

Furthermore, it is preferred if a DC/DC converter is used in the motor energization device, which is additionally integrated in the actuating unit in order to increase the voltage supplied by the energy storage unit from 12 VDC to 36 VDC, which is the voltage required to operate a converter-fed permanent-magnet synchronous motor.

Here, it is preferred if the use of a boost converter replaces two of the three battery packs previously required to power a surgical device that requires, for example, an input voltage of 36 VDC. This has the advantage of considerable cost saving, since the rough calculation on ions shows that the cost of a series boost converter is significantly, in particular 10 times, lower than the cost of two battery packs.

Furthermore, it is preferred that a free adjustment of the voltage amplification enables the use of any battery technology. This has the advantage that this flexibility eliminates dependence on individual suppliers or possible discontinued products. In addition, the weight of the converter is considerably less than the weight of the batteries. This results in an improvement in the handling of the device. A low overall weight is especially important in particular for devices that have to be held directly by the operator.

In addition, for a given size and a given volume, the invention allows the motor to operate at a significantly higher voltage level. This results in a significantly lower current level, higher efficiency and lower cost of motor production.

Furthermore, drive systems in operating rooms for bone treatment, for example, are either for battery-powered motors corresponding to a 12 V supply or for wired systems corresponding to a 36 V supply. The invention has the advantage that the two motor platforms can be reduced to one platform.

By reducing the size of the battery or of the energy storage unit, the charging time is reduced accordingly. It is important to note that although the stored energy is reduced to one third of the original capacity, the available charge should easily survive a normal surgical procedure.

Furthermore, it is preferred that a further variant of the invention is housed in a power tool. An inverter/DC bus with 36 VDC is used for driving the permanent-magnet synchronous motor. This solution would drastically increase the handling of these instruments.

Due to important and possibly fluid-sensitive components integrated in the switch housing of the actuating unit, it is advantageous if the switch housing is fluid-tight or can be sealed in a fluid-tight manner.

A further advantage of the aforementioned embodiment is the significant reduction in space requirements in an operating room due to the complete/entire omission of the control and/or monitoring unit as an external device. An advantage can also be achieved by using only one cable, which preferably has half the total cable length of the lines from the prior art described above. The reduced cable length ensures safer and less susceptible transmission of safety-relevant electrical signals and data or operating parameters.

Furthermore, it is preferred if the energy storage unit is an accumulator/rechargeable battery or a battery. More preferred is the use of an accumulator, which is rechargeable and thus less costly as well as more environmentally friendly than a battery. Another advantage of an integrated accumulator is that the cable/line for powering the energy storage unit can be omitted. This allows the entire system to be operated in a sterile area without the power supply cable breaking a bridge between the sterile area and the non-sterile area. Such an embodiment allows the energy storage unit to be replaced or charged in the absence of a patient, i.e. in an offline operating mode.

It is further preferred if the IPU unit is configured to centrally acquire data and/or operating parameters in the actuating unit, in particular the foot-operated switch unit or hand-operated switch unit. In other words, a central data acquisition apparatus is provided in the foot-operated switch unit or hand-operated switch unit, which can receive, store and, if necessary, output the data. Thus, the data can be accessed both in the operating mode and in the offline operating mode. Furthermore, by such a central data acquisition, all data acquired in a more or less extended area are combined at a central location. In this way, different communication or sending paths between several data acquisition apparatuses can be dispensed with.

It is further preferred if the IPU unit has a data interface, in particular an interface for plugging in a storage medium, for reading all data and/or operating parameters, preferably the motor history of all application parts/handpieces. Thus, the present subject matter of the invention offers the possibility to access the stored and/or acquired data and/or operating parameters of the IPU unit in an offline operating mode by plugging a storage medium to the IPU unit, in order to subsequently read, process or further use them, for example, on a separate device, preferably independent of the IPU unit, such as a PC/computer. Such a storage medium can be, for example, a USB stick, a memory card or the like.

Furthermore, it is preferred if the IPU unit can be completely removed/detached from the switch housing, in particular for cleaning and/or reprocessing the switch housing, and can then be used again. In addition to cleaning and/or reprocessing, especially of the outer surfaces of the actuating unit, it is also conceivable to connect the IPU unit to a computer, for example, in order to be able to access the data and/or operating parameters stored/recorded on it. Furthermore, in this way it is possible to upload/install necessary updates and/or new programs. Another advantage is that the switch housing can be subjected to more intensive cleaning if the IPU unit is not in the switch housing at that time.

It is furthermore preferred if the underside of the switch housing is provided with a non-slip coating. This has the advantage that the actuating unit does not slip when it is operated by an operator, preferably hospital staff, in particular an operating surgeon. This can also prevent, for example, the pressure force to be applied by the operator from varying, as would be the case if, for example, the switch housing did not rest on the surface, preferably the bottom, in a slip-resistant manner. Furthermore, it is advantageous if the actuating element does not change its position even in the event of unintentional contact, for example an impact from the side. Nevertheless, it is provided that the actuating unit remains a mobile unit that can always be positioned as desired and is not firmly connected to the surface/bottom.

It is furthermore preferred if bidirectional data exchange is provided between the IPU unit and a charging device during a charging process and data exchange, in particular of all data and/or operating parameters of all application parts, is provided between the charging device and a cloud. By storing all or only some of the data and/or operating parameters in a cloud, it is also possible to retrieve this data outside of and in the absence of the IPU unit. A bidirectional data exchange means here that a data transmission takes place in both directions between two devices. This means that both devices are able to receive data (receiver) as well as to send data (transmitter). In order to be able to guarantee this, it is understood that the corresponding interfaces are also configured bidirectionally.

It is furthermore preferred if communication of the actuating unit with a smartphone or tablet is provided, in particular for operating the respective application part and for use as a display of the IPU unit. In this way, the smartphone or tablet can be used to check the state of charge of the integrated energy storage unit and/or to switch the power supply on or off, i.e. to put the actuating unit into operation or to switch to the offline operating mode. Furthermore, it is possible in this way to use various settings, such as setting individual motor parameters, or individual operation of the application parts. The communication connection from the smartphone or tablet to the actuating unit is wireless, preferably via Wi-Fi. Alternatively, there is the possibility of data transmission via Bluetooth.

Furthermore, the present invention relates to a surgical treatment system comprising an electromotively-operated surgical instrument, whose electric motor, which is configured for operation with an energy storage unit, is housed in a handpiece, at the proximal end or end region of which a cable connection for the power supply of at least the electric motor and/or for the transmission of data and/or operating parameters is formed or arranged, and an actuating unit having the features according to one of the preceding aspects.

Thus, the aforementioned object of the invention as well as the surgical treatment system offers significant space savings in the operating room as well as cost reductions compared to already known setups. Furthermore, the actuating unit is a compact, lightweight and moreover mobile unit.

BRIEF DESCRIPTION OF THE DRAWING FIGURES

FIG. 3 is an illustration showing a treatment system according to the present disclosure;

FIG. 4 is an illustration showing the treatment system according to the prior art.

DETAILED DESCRIPTION

The following describes configuration examples of the present disclosure based on the accompanying figures. The figures are merely schematic in nature and are provided for the purpose of understanding the invention. The same elements are designated by the same reference signs.

Figure 1:
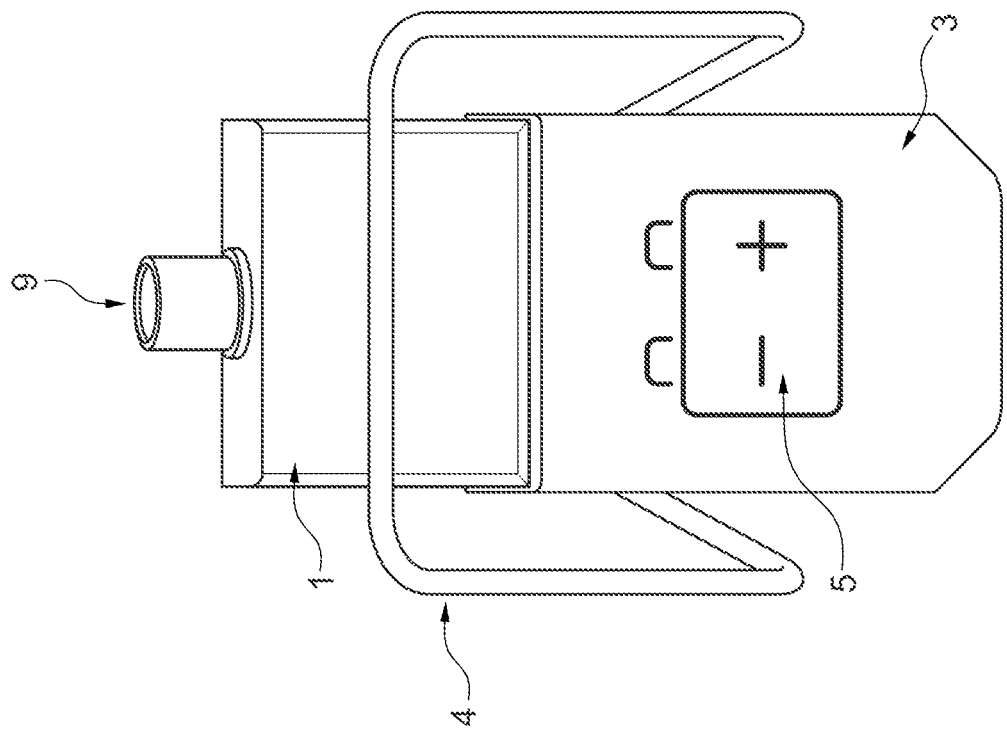
FIG. 1 is an illustration showing the actuating unit according to the present disclosure.

FIG. 1 is an illustration showing the actuating unit 1 according to the present disclosure. In FIG. 1, according to a preferred embodiment, the actuating unit 1 is configured as a foot-operated switch unit to be/come in contact with an electromotively-operated surgical instrument 2 (see FIG. 3). Accordingly, a hand-operated switch unit is similarly configured. The actuating unit 1 has a switch housing 3 formed with a frame 4. The frame 4, which is formed as a fixed bracket above the switch housing 3 and is fixed/attached to the switch housing 3 on two opposite sides, is used for lifting and moving the actuating unit 1 by an operator, preferably with his foot/hand. The top side of the switch housing 3 of the actuating unit 1 is pressed towards the bottom/support surface when actuated. The actuating unit 1 is provided with a power supply unit 5, which supplies power/energy to a motor system 6 (see FIG. 3) connected to it. In addition, a cable connection is provided for attaching a cable 8 (see FIG. 3) on one side of the actuating unit 1.

Figure 2:
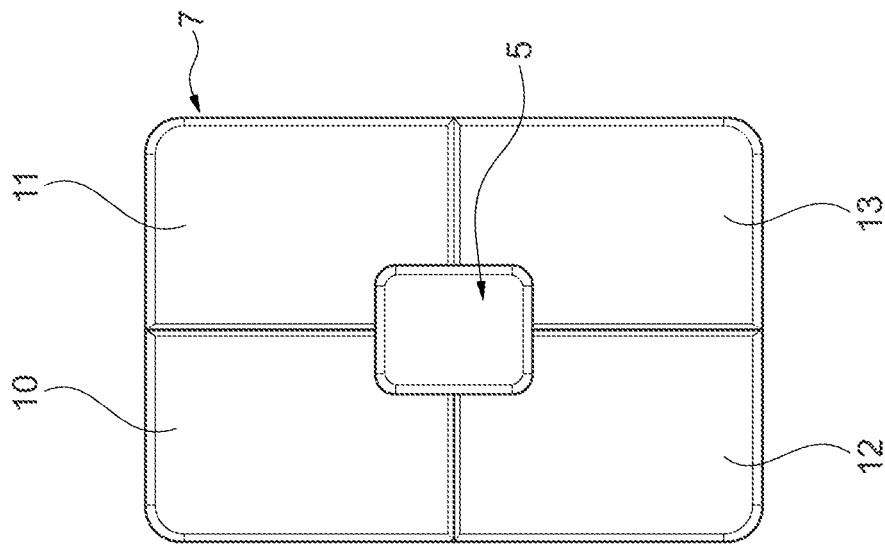
FIG. 2 is an illustration showing the control and monitoring unit according to the present disclosure.

FIG. 2 is an illustration showing the control and monitoring unit 7 according to the present disclosure. The control and monitoring unit 7 is provided to be integrated into the switch housing 3 according to FIG. 1. The control and monitoring unit 7 is a preferably completely removable IPU unit 7, consisting of a plurality of partial components. In FIG. 2, it can be seen that the IPU unit is formed with a signal-generator apparatus 10, a motor energization apparatus 11, a data acquisition apparatus 12 and a sending unit 13. In addition, the IPU unit has an energy storage unit 5, preferably formed as an accumulator, which is preferably provided centrally in the IPU unit 7 and which supplies the surrounding partial components as well as the motor system 6 with energy/power for electromotive operation of the surgical instrument 2. It is preferred if the IPU unit 7 has almost the same shape as the switch housing 3 of the actuating unit 1.

FIG. 3 is an illustration showing a treatment system according to the present disclosure. The treatment system has the actuating unit 1 already described in FIG. 1, in which the IPU unit 7 with the energy storage unit 5 is integrated. The motor system 6 is connected at its proximal end 17 to the cable connection 9 of the actuating unit 1 via a cable 8. The motor system 6 is connected at its distal end 18 to the surgical instrument 2. The motor system 6 and the surgical instrument 2 connected to it together form the handpiece/application part 14.

In addition, it is provided that the IPU unit 7 is connected wirelessly to a smartphone 16 via a communication connection 15. The communication connection 15 is configured in such a way that, for example, adjustments of individual motor parameters can be made. Furthermore, it is preferred if the display of the smartphone 16 is used as the display of the IPU unit 7. This means that the smartphone 16 can be used, for example, to read the state of charge of the energy storage unit and/or to switch the energy supply on and off.

FIG. 4 is an illustration showing the treatment system according to the prior art. FIG. 4 is essentially the same as the illustration in FIG. 3, with the difference that in the prior art, three cables have to be used to perform all the necessary and/or desired functions in order to operate the surgical instrument 2. Thus, in FIG. 4, a first line 19 can be seen, which is a supply line between a power supply or mains (not shown) and a control and monitoring device 7. The second line 20 connects the control and monitoring device 7 to the motor system 6 integrated in the application part 14, which is connected to the surgical instrument 2. The third line 21 is used to connect the control and monitoring device 7 to the actuating unit 1.

A comparison of the two FIGS. 3 and 4 shows that the one cable 8 according to FIG. 3 replaces both the first line 19, the second line 20 and the third line 21. This eliminates the need for cables/lines running across the operating room.

Figure 5:
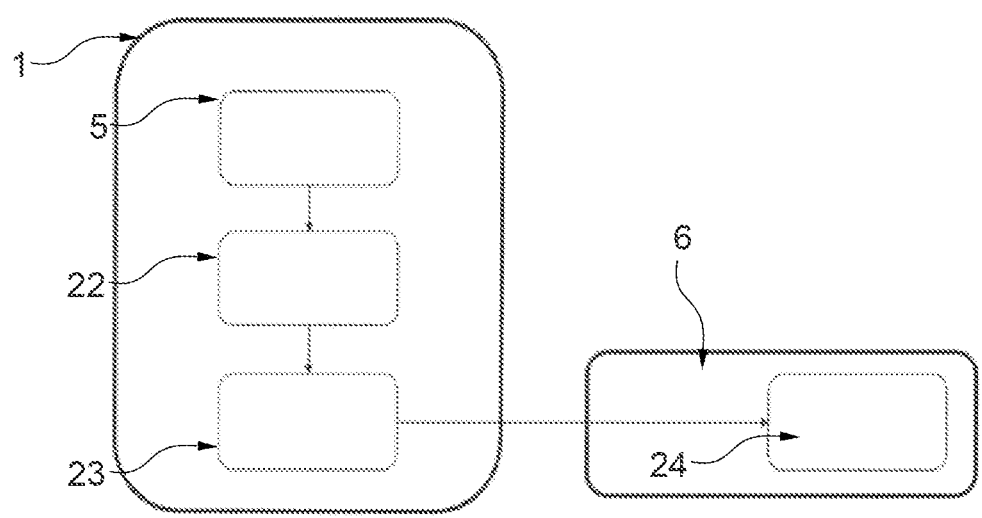
FIG. 5 is an illustration showing the power supply components of the motor system.

FIG. 5 is an illustration showing the power supply components of the motor system. FIG. 5 shows the power supply unit 5, a converter 22 and an inverter 23, which are integrated in the actuating unit 1. Here, it is preferred that the converter 22 and the inverter 23 are part of the motor energization device 11. The energy storage unit 5 supplies a 12 V direct current voltage to the converter 22, which converts the 12 V direct current voltage into 36 V direct current voltage. The 36 V direct current voltage from the converter is output to the inverter 23, which converts it to an alternating current voltage and outputs it to the motor system 6 in order to energize or drive the permanent-magnet synchronous motor 24 integrated therein.

The invention claimed is:

1. An actuating unit for an electromotively-operated surgical instrument, the actuating unit comprising:
   A. a switch housing that is separate from and spatially spaced apart from the surgical instrument, the switch housing comprising a frame and a support;
   B. at least one power supply unit configured for supplying power to at least one motor system of the surgical instrument;
   C. a control and monitoring device configured to perform and/or monitor at least one of the following functions:
      receiving and/or sending data to an external instrument-actuating unit,
      outputting and/or receiving operating parameters and operating signals to/from the surgical instrument, and
      storing data and/or operating parameters; and
   D. a cable connection for electrically coupling the actuating unit to the surgical instrument for operating the motor system via the at least one power supply unit integrated in the actuating unit,
   the control and monitoring device being integrated into the switch housing and comprising an IPU unit,
   the at least one power supply unit being integrated in the IPU unit and configured to supply energy to the electromotively-operated surgical instrument and components of the control and monitoring device,
   the actuating unit further comprising a communication connection of the IPU unit with a smartphone or tablet for operating a handpiece/application part and for use as a display of the IPU unit,
   the IPU unit configured to monitor a state of charge of the at least one power supply unit and/or to switch an energy supply on and off as well as set individual motor parameters via the smartphone or tablet.

2. The actuating unit according to claim 1, wherein the IPU unit comprising the at least one power supply unit, and the components of the control and monitoring device are as follows: a signal-generator device, which is configured to output the operating parameters and operating signals to the motor system, a motor energization device, which is configured to control current in the motor system, a central data acquisition device which is configured to receive, store, acquire, and output the data and/or operating parameters of the handpiece/application part which include a motor system and a surgical instrument connected to it together and a sending unit, which is configured to send the data and/or operating parameters to a smartphone or tablet, and the IPU unit is integrated in the switch housing of the actuating unit.

3. The actuating unit according to claim 2, wherein the IPU unit is configured to centrally acquire data and/or operating parameters in the switch housing of the actuating unit.

4. The actuating unit according to claim 2, wherein the IPU unit has a data interface for reading all data and/or operating parameters of a motor history of all application parts.

5. The actuating unit according to claim 2, wherein the IPU unit is completely removable from the switch housing.

6. The actuating unit according to claim 5, wherein the IPU unit is configured to be plugged into a computer to access data and/or operating parameters stored on and/or acquired by the IPU unit.

7. The actuating unit according to claim 6, wherein the IPU unit is adapted to install necessary updates and/or new programs.

8. The actuating unit according to claim 2, wherein a bidirectional data exchange is provided between the IPU unit and a charging device during a charging process, and wherein another data exchange is provided between the charging device and a cloud.

9. The actuating unit according to claim 1, wherein the at least one power supply unit is an accumulator or a battery.

10. A surgical treatment system comprising:
    the actuating unit according to claim 1; and
    an electromotively-operated surgical instrument comprising a motor system configured for operation with the at least one power supply unit, the motor system being housed in an application part, and the cable connection being arranged at a proximal end or end region of the application part.

* * * * *